United States Patent [19]
Kelkar et al.

[11] Patent Number: 5,518,704
[45] Date of Patent: *May 21, 1996

[54] NICKEL AND COBALT CONTAINING HYDROTALCITE-LIKE MATERIALS HAVING A SHEET-LIKE MORPHOLOGY AND PROCESS FOR PRODUCTION THEREOF

[75] Inventors: Chandrashekhar P. Kelkar, Plum Boro; Alain A. Schutz, Monroeville Boro; Leonard A. Cullo, Hempfield Township, Westmoreland County, all of Pa.

[73] Assignee: Aristech Chemical Corporation, Pittsburgh, Pa.

[*] Notice: The term of this patent shall not extend beyond the expiration date of Pat. No. 5,399,329.

[21] Appl. No.: 407,556

[22] Filed: Mar. 20, 1995

Related U.S. Application Data

[63] Continuation-in-part of Ser. No. 85,804, Jul. 6, 1993, Pat. No. 5,399,329.

[51] Int. Cl.$^6$ ....................................... C01B 31/30
[52] U.S. Cl. ........................ 423/420.2; 556/28; 556/31
[58] Field of Search ........................ 423/420.2; 556/28, 556/31

[56] References Cited

U.S. PATENT DOCUMENTS

| | | | |
|---|---|---|---|
| 3,796,792 | 3/1974 | Miyata et al. | 423/250 |
| 4,351,814 | 9/1982 | Miyata et al. | 423/306 |
| 4,458,026 | 7/1984 | Reichle | 502/80 |
| 4,970,191 | 11/1990 | Schutz | 502/341 |
| 5,064,804 | 11/1991 | Soo et al. | 502/335 |
| 5,202,496 | 4/1993 | Schutz et al. | 568/388 |

OTHER PUBLICATIONS

D. C. Puxley et al, "The Effect of Preparation Method upon the Structures, Stability & Metal/Support Interactions in Nickel/Alumina Catalysts", Preparation of Catalysis III, G. Poncelet et al (Editors), 1983 Elsevier Science Publishers B. V., Amsterdam—Printed in the Netherlands, pp. 237–271.

Luis E. Alzamora et al, "Coprecipitated Nickel–Alumina Catalysts for Methanation at High Temperature", Part 2—Variation of Total & Metallic Areas as a Function of Sample Composition & Method of Pretreatment, J. Chem. Soc., Faraday Trans. I, 1981, 77, pp. 665–681.

*Primary Examiner*—Wayne Langel
*Attorney, Agent, or Firm*—William L. Krayer; Robert R. Gavlik

[57] ABSTRACT

A synthetic nickel (or cobalt) containing hydrotalcite-like material having a sheet-like morphology and a sheet broadness to thickness ratio of at least 50 and a formula $M_{1-x}Al_x(OH)_2 \cdot xA \cdot mH_2O$ where M is Ni or Co, A is a mono carboxylic anion of the form $RCOO^-$ where R is $C_nH_{2n+1}$ and n=0–5, and x and m are numbers satisfying the following conditions:

$$0.2 <= x <= 0.4$$

$$0.0 <= m <= 4$$

It is made by starting with a synthesis mixture having Ni or Co (divalent cation) to aluminum (trivalent cation) molar ratio between 1:1 and 10:1, mono carboxylic anion to aluminum (trivalent cation) molar ratio between 0.1:1 to 1.2:1 and optionally added other anions. The process comprises of reacting a mixture comprising nickel (or cobalt) and aluminum cations and mono carboxylic anions in an aqueous slurry at a temperature of at least 40° C. and a pH of at least 7.

23 Claims, 6 Drawing Sheets

NICKEL AND COBALT CONTAINING HYDROTALCITE-LIKE MATERIALS HAVING A SHEET-LIKE MORPHOLOGY AND PROCESS FOR PRODUCTION THEREOF

RELATED APPLICATION

This is a continuation-in-part of our co-pending application Ser. No. 085,804, filed July 6, 1993, entitled "Hydrotalcite-like Materials Having a Sheet-like Morphology and Process for Production Thereof", U.S. Pat. No. 5,399,329.

TECHNICAL FIELD

This invention relates to nickel and cobalt containing hydrotalcite-like compounds having a unique sheet like morphology, defined as broad and thin crystals having a breadth to thickness ratio of more than 50 and to a process for the production thereof. These hydrotalcite-like materials have applications in new fields as well as conventional applications, arising from their unique sheet crystal morphology and derived physico-chemical properties.

BACKGROUND OF THE INVENTION

Hydrotalcite is a naturally occurring mineral having the formula:

$$Mg_6Al_2(OH)_{16}CO_3 \cdot 4H_2O$$

Several other cation pairs forming hydrotalcite-like structure also occur in nature and of particular interest for the purposes of the present invention is takovite, the nickel analog of hydrotalcite having the formula:

$$Ni_6Al_2(OH)_{16}CO_3 \cdot 4H_2O$$

Hydrotalcite-like materials or anionic clay minerals have similar structures and have the general formula:

$$[M^{II}_{1-x}M^{III}_x](OH)_2 \cdot {}^{x}\!/_y A^{y-} \cdot mH_2O$$

where $M^{II}$ and $M^{III}$ are divalent and trivalent cations, respectively, and A is an anion. These materials belong to the pyroaurite-sjogrenite class of minerals and their crystal structure has been described in the literature (Allmann, R., *Acta Cryst.* (1968), B24, 972). They have been widely described in the literature (Cavani et al., *Catalysis Today*, 11, 173(1991) and references therein). Although, the word hydrotalcite refers specifically to the Mg-Al mineral, in the catalyst literature, it encompasses all the materials in the pyroaurite-sjogrenite class. Hence for the purposes of this invention, the term hydrotalcite will include materials containing nickel or cobalt and aluminum. The most common approach to synthesis of nickel (or cobalt) hydrotalcites is by coprecipitation of the two cations under conditions of supersaturation (U.S. Pat. No. 3,896,053, 3,941,721, 4,105,591, 4,298,766) and references therein. It is well known that hydrotalcites prepared by the above procedures have a hexagonal plate-like crystal habit (Reichle, W. T., Chemtech, 1986, 58). When crystallized at room temperature the crystallites have a diameter of approximately of about 0.01 to 0.1 microns and can be grown to about 1 to 5 microns by hydrothermal treatment. In all cases, the ratio defined by the diameter to the thickness of hexagonal crystals in such synthetic materials of the prior art are in the range of about 5 to about 20. Scanning and transmission electron microscope (TEM) pictures of hydrotalcite with the hexagonal plate-like crystal morphology are shown in FIGS. 1a and 1b, respectively.

The term "hydrotalcite-like" is recognized in the art. It is defined and used in a manner consistent with usage herein in the comprehensive literature survey of the above-referenced Cavani et al article.

SUMMARY OF THE INVENTION

We worked on synthesizing nickel (or cobalt) containing hydrotalcites using variations in the nickel or cobalt and aluminum compounds and more importantly, with mono carboxylic organic acids such as formic, acetic, propionic and isobutyric, having the following formula:

$$M_{1-x}Al_x(OH)_{2+x-y-nz} \cdot yA^- \cdot zB^{n-} mH_2O$$

where M is either Ni or Co, A' is a mono carboxylic anion, B is OH or an optionally added anion or a combination of anions, x, y, z and m are numbers satisfying the following conditions:

$$0.2 < x \leq 0.4$$

$$0.1 < y \leq 0.5$$

$$0 < z \leq 0.4$$

$$1 \leq n \leq 3$$

From the above it will be seen that, where B is not present, (where z=0), the basic formula of our materials is $M_{1-x}Al_x(OH)_{2-xA}^- \cdot mH_2O$. The mono carboxylic anion $A^-$ may be substituted by one or more different anions having an average valence of n, up to about 90 mole percent. We discovered that hydrotalcite-like materials with a sheet-like morphology (hereafter referred to as "sheet hydrotalcites") are generally crystallized when monocarboxylic anions are used, for balancing the positively charged hydroxide structure, in the synthesis. Electron microscope photographs of the new materials are shown in FIGS. 2a, 2b, 3a and 3b. Interestingly dicarboxylic acids and other polycarboxylic acid compounds will not operate to make the sheet hydrotalcite-like materials of our invention.

It was also found that such new crystal morphology could also be formed when nickel (or cobalt) was partially (up to about 50 mole percent) substituted from a family of cations consisting essentially of Mg, Ni, Co, Zn, Cu, Mn; and aluminum was partially (up to about 50 mole percent) substituted from a family of cations consisting essentially of Cr and Fe. After one sheet material is made, a portion of the anions may be exchanged for other anions.

It has been found that the sheet hydrotalcite has several useful characteristics arising from the sheet crystal habit. In contrast to typical hydrotalcite materials, having the hexagonal plate-like crystal morphology, the new sheet material can be shaped or formed without binders into shapes which retain their mechanical strength even after calcination to high temperature.

It is the object of the present invention therefore to provide novel sheet hydrotalcite materials.

It is also the object of this invention to provide a process for producing the sheet hydrotalcites in a commercially advantageous manner.

DETAILED DESCRIPTION OF THE INVENTION

Figure 1A:
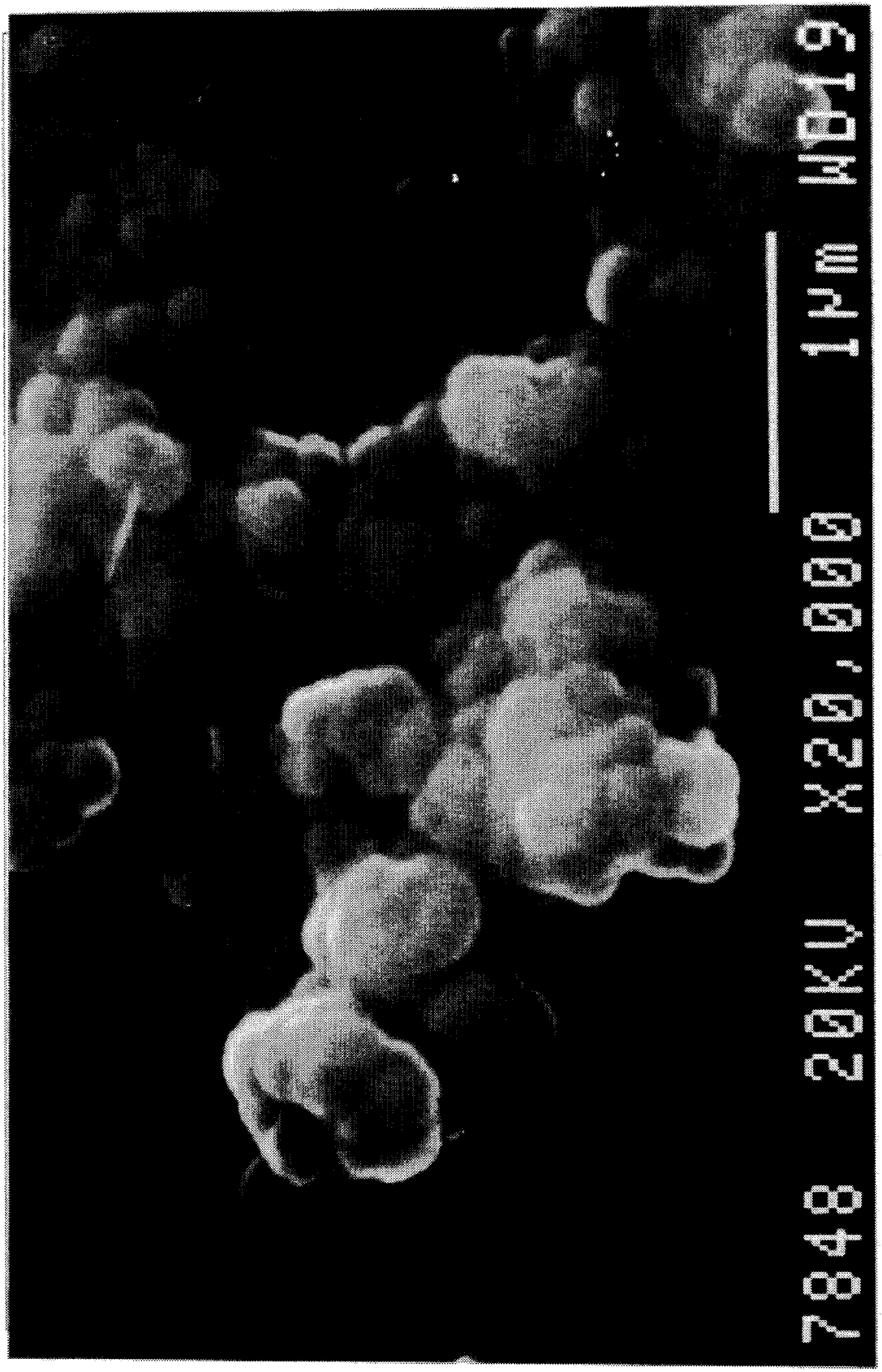
FIG. 1a is the scanning electron microscope picture of a conventional hexagonal nickel hydrotalcite known in prior art taken at 20,000× (Comparative Example 1).
Figure 2A:
FIG. 2a is the scanning electron microscope picture of the sheet nickel-hydrotalcite produced according to this invention using acetic acid taken at 1800× (Example 1).
Figure 3A:
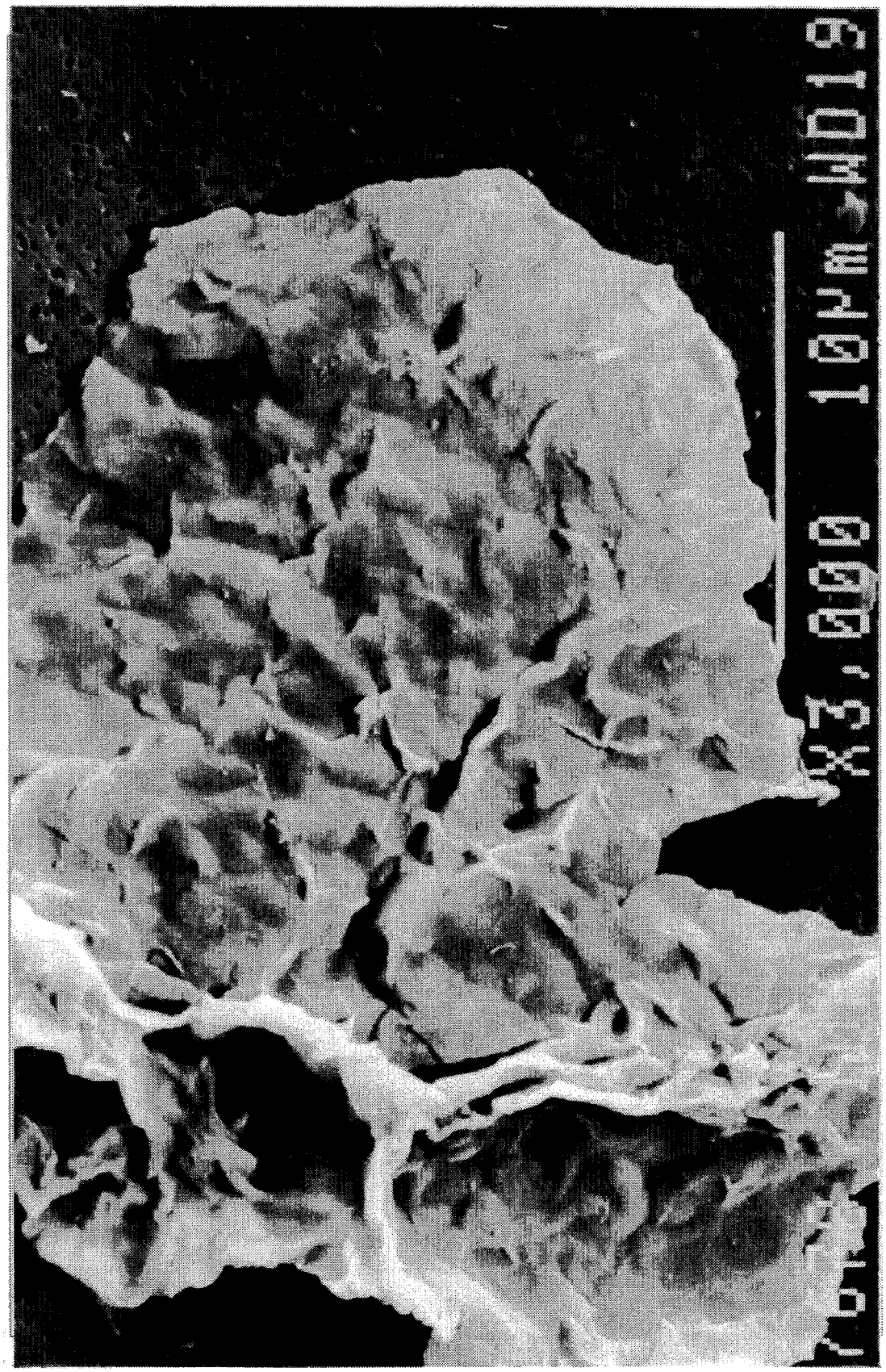
FIG. 3a is a scanning electron microscope picture of the sheet cobalt-hydrotalcite produced according to this invention using acetic acid taken at 3000× (Example 6).

A comparison of FIGS. 1a with 2a and 3a shows that the nickel (or cobalt) hydrotalcite of this invention differs from the conventional hydrotalcite having a hexagonal plate-like structure. As seen from FIG. 2a, the longitudinal dimension of the sheet is much larger than the thickness. The ratio is so large that the sheets are pliable and are crumpled. The longitudinal dimensions of the sheets can be relatively accurately measured from SEM pictures (FIGS. 2a, 3a). As seen from FIG. 2a, the ratio of the maximum longitudinal dimension to the minimum longitudinal dimension is less than 5. More often the ratio is very close to unity. In the discussion which follows the breadth of the sheets will refer to the maximum longitudinal dimension. The breadth was calculated by averaging the maximum longitudinal dimension of at least ten different sheet crystallites. The sheet hydrotalcite of the present invention has sheets where the breadth ranges from about 5–500 microns.

The thickness of the sheets is estimated from the specific surface area and the density. The thickness of the sheets is calculated from the following equation:

$$\text{thickness} = \frac{2}{\text{surface area} \times \text{density}}$$

where the surface area is measured by BET method and the density of the hydrotalcite-like materials can be calculated for different cation pairs and anions by crystallographic means. The skeletal densities calculated for hydrotalcite-like material having the Ni (or Co), Al cation pair in a molar ratio of 2.0:1 of M/Al, where M is Ni or Co, dried overnite at 60° C. with different anions in the interlayer, are listed in the table below.

TABLE

| Skeletal Densities of Different Hydrotalcite-Like Materials (g/cc) | |
| --- | --- |
| Ni—Al-formic | 2.61 |
| Ni—Al-acetic | 2.25 |
| Ni—Al-propionic | 1.73 |
| Ni—Al-isobutyric | 1.62 |
| Co—Al-formic | 2.61 |
| Co—Al-acetic | 2.25 |
| Co—Al-propionic | 1.73 |
| Co—Al-isobutyric | 1.62 |

Based on the above formula, the thickness of the sheet hydrotalcite-like material of the present invention is calculated to be about 0.005 to 0.1 microns. Therefore the ratio of breadth to thickness of the sheet hydrotalcite-like materials of the present invention is at least 50, generally up to about 5000, and more typically of the order of 500–1500.

The sheet hydrotalcites of the present invention are made by contacting an aluminum compound with a nickel (or cobalt) compound in water, together with a carboxylic acid having up to 6 carbon atoms. The aluminum source can be in the form of a reactive oxide, hydroxide, anionic salt or a mono carboxylic acid salt, the preferred source of aluminum being sodium aluminate or pseudoboehmite with pseudoboehmite being the most preferred. Inorganic salts of the trivalent cation, e.g. aluminum nitrates, are not preferred for use as a source for the present invention. The nickel (or cobalt) source may be in the form of oxide, hydroxide or a mono carboxylic acid salt, the most preferred source being the hydroxide. Inorganic salts of the divalent cation, e.g. nickel (or cobalt) nitrate are not preferred for use as a source for the present invention. The nickel (or cobalt) source is added such that the molar ratio of divalent to trivalent metal is about 1:1 to 10:1; preferably between 2:1 and 4:1. The amount of water soluble mono carboxylic acid equivalents is added such that the ratio of organic acid anion to trivalent cation is preferably 1:1 on a molar basis but may vary from 0.1:1 to 1.2:1. In cases where the ratio is less than unity the rest of the charge is balanced by hydroxyl anions present in the synthesis medium. Optionally, an inorganic anion or a combination of inorganic anions may also be present in the synthesis mixture, in which case they are incorporated into the layers instead of the hydroxyl ions. In any case it is preferred for the purposes of the present invention that at least 10 mole percent of the anions in the synthesis mixture be monocarboxylic anions. The mono carboxylic acid equivalents are added either in the form of the acid or as salts of any of the combination of cations being used. The final pH of the synthesis mixture should be between 7 and 12 but preferably between 8 and 9. Heating and mixing the above reaction mixture will facilitate the crystallization reaction. The reaction time can extend from 0.5 h to several hours, i.e. as much as 72 h or more depending on the reaction temperature and mixing. The crystallization is carried out at a temperature of at least 40° C. and atmospheric pressure. The rate of crystallization can be accelerated by increasing the temperature. The synthesis can also be carried out at higher than atmospheric pressures in a closed system, in which case the temperature can exceed 100° C. and the time of reaction is further shortened. The preferred crystallization temperature is about 60° to 100° C. but more preferably between 85° and 95° C. and at atmospheric pressure. After the crystallization period, the product consists of a thick homogeneous slurry.

It was also discovered that the hydrotalcites of the present invention could also be synthesized starting from the hexagonal hydrotalcites. It is known in the literature that calcined hydrotalcite-like materials have the capacity to reconstitute the original layered structure upon exposure to water (U.S. Pat. No. 5,079,203). The temperature of calcination is critical and should not exceed 500° C. We discovered that if the calcined hexagonal hydrotalcite-like material is recrystallized in a aqueous solution containing a monocarboxylic organic anion of the form $RCOO^-$, where R is $C_nH_{2n+1}$ and n is an integer from 0 to 5, sheet hydrotalcite-like material is reconstituted. This route provides a method of transforming the hexagonal hydrotalcite made by other methods to the sheet hydrotalcite-like material of the present invention.

It is clear from the present invention that the presence of a water soluble mono carboxylic anion is the key in the synthesis of sheet hydrotalcite.

A dried sample of the slurry shows an X-ray diffraction pattern characteristic to hydrotalcite materials but with expanded d-spacing due to the larger size of the intercalated organic anions. Typical X-ray diffraction lines of a crystalline sheet hydrotalcite made with acetic acid have been identified and are shown in Table 1.

TABLE 1

Powder diffraction pattern of sheet hydrotalcite synthesized in Example 1 dried at room temperature. Spacings in Å.

| d spacing (Å) | Relative Intensity | Miller Indices |
| --- | --- | --- |
| 12.50 | 100 | 0,0,3 |
| 6.46 | 22 | 0,0,6 |
| 4.22 | 37 | 0,0,9 |
| 3.08 | 4 | 0,0,12 |
| 2.57 | 14 | 0,1,5 |
| 2.36 | 13 | 0,1,8 |
| 1.51 | 14 | 1,1,6 or 1,1,0 |

The crystallinity of the material can vary depending on the reaction temperature, time and mixing. Most of the sheet hydrotalcites, according to this invention, show diffraction patterns with strong 00l lines and weak and sometimes ill-defined hk0 lines. Again this is the result of the unique morphology of the crystals. An easy characterization of crystallinity consists of depositing a few drops of synthesis suspension on a glass slide, drying and analyzing by X-ray diffraction. As commonly used with layered structures, this method orients the crystals and enhances the 00l lines. Several d(003) spacings, obtained with different mono carboxylate anions are shown in Table 2. Samples for scanning electron microscopy were prepared by freeze drying the slurry to prevent the rolling up of sheets as would normally occur in a regular drying process.

TABLE 2 d(003) spacings for several sheet hydrotalcites made with different organic acids and dried at 60° C.

| Carboxylic Anion | d(003) Spacing Å | Example |
| --- | --- | --- |
| Formic | 7.64 | 1 |
| Acetic | 12.3 | 2 |
| Propionic | 13.02 | 3 |
| Isobutyric | 15.15 | 4 |

EXAMPLE 1

Figure 2B:
FIG. 2b is a transmission electron microscope picture of the sheet nickel-hydrotalcite produced according to this invention using acetic acid taken at 50,000× (Example 1).

15.5 g of pseudoboehmite (Versal 850) was slurried in 500 ml of deionized water. 13.7 g of acetic acid was added to the slurry. The suspension was vigorously agitated and heated to 50–60° C. for 0.5 h. Then 40.9 g of nickel hydroxide along with 1.5 l of deionized water were added to the resulting mixture and heated to 85°–95° C. for 6 hours. The ratio of nickel to aluminum in the mixture was 2:1 and the ratio of carboxylic anion to aluminum was 1:1. A portion of the final slurry was dried at 60° C. and X-ray diffraction carried out to confirm the hydrotalcite phase. TEM was performed on another portion of the slurry to confirm the presence of sheet hydrotalcite (FIG. 2b). Surface area of a sample dried and conditioned at 150° C. was about 35 m²/g, which corresponds, using the relationship described above, to about 0.02 micron in thickness. The average breadth of the sheets was determined from SEM pictures (FIG. 2a) to be 20 microns, yielding a ratio of breadth to thickness of 1000.

COMPARATIVE EXAMPLE 1

Figure 1B:
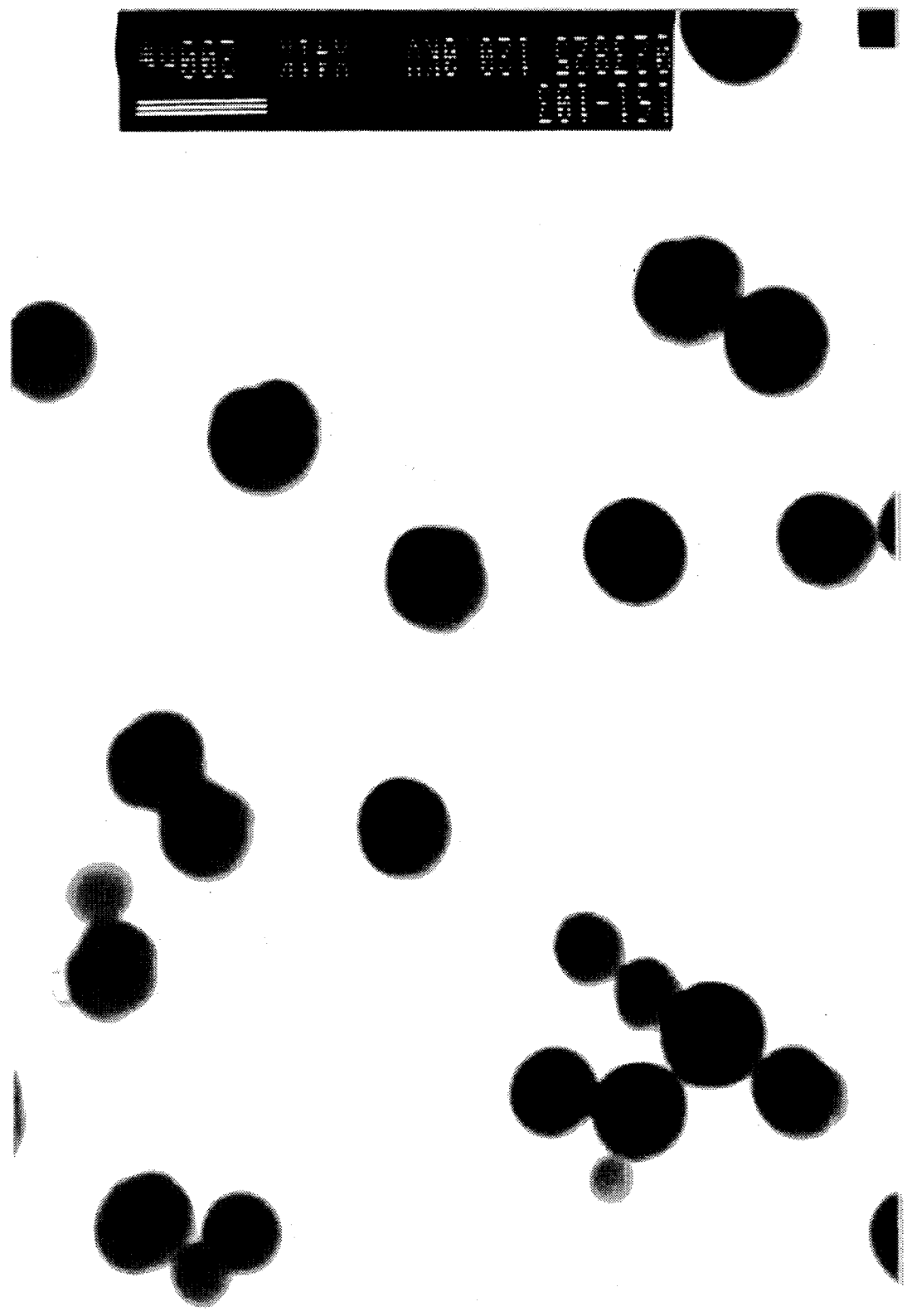
FIG. 1b is the transmission electron microscope picture of the same hydrotalcite taken at 41,000×.

A mixture of 20.6 g of aluminum nitrate and 32.15 g of nickel nitrate were dissolved in 300 ml of deionized water. A separate solution of 10.15 g sodium hydroxide pellets dissolved in 500 cc of DI water was prepared. The two solutions were coprecipitated at a constant pH of 9.0 with vigorous stirring. Upon completion of addition the slurry was heated to 80° C. for 16 h. After cooling the slurry was washed to remove the excess salt. The procedure described above substantially follows the description in the prior art for making nickel hydrotalcite. A portion of the final slurry was dried at 60° C. and X-ray diffraction carried-out to confirm the hydrotalcite phase. The TEM pictures clearly show the hexagonal crystallites (FIG. 1b). The SEM pictures distinctly show clustered, individual platelets which are approximately 0.5 micron in diameter (FIG. 1a).

EXAMPLE 2

14.9 g of pseudoboehmite (Versal 850) was slurried in 500 ml of deionized water. 19.3 g of isobutyric acid was added to the slurry. The suspension was vigorously agitated and heated to 50°–60° C. for 0.5 hour. Then 40.8 g of nickel hydroxide along with 1.5 l of deionized water were added to the resulting mixture and heated to 85°–95° C. for 6 hours. The ratio of nickel to aluminum in the mixture was 2:1 and the ratio of carboxylic anion to aluminum was 1:1. A portion of the final slurry was dried and the presence of hydrotalcite-like phase confirmed by X-ray diffraction. Another portion of the final slurry was freeze dried and the sheet morphology confirmed by SEM. Transmission electron microscopy also shows the presence of sheet hydrotalcite-like material.

EXAMPLE 3

15 g of pseudoboehmite (Versal 850) was slurried in 500 ml of deionized water. 13.7 g of acetic acid was added to the slurry. Then 61.3 g nickel hydroxide along with 1.5 l of deionized water were added to the resulting mixture and heated to 85°–95° C. for 6 hours. The ratio of nickel to aluminum in the mixture was 3:1 and the ratio of carboxylic anion to aluminum was 1:1. A portion of the final slurry was dried and the presence of hydrotalcite-like phase confirmed by X-ray diffraction. Another portion of the final slurry was freeze dried and the sheet morphology confirmed by SEM.

EXAMPLE 4

15.13 g of pseudoboehmite (Versal 850) was slurried in 500 ml of deionized water. 13.7 g of acetic acid was added to the slurry. The suspension was vigorously agitated and heated to 50–°60° C. for 0.5 h. 81.7 g nickel hydroxide along with 1.5 l of deionized water were added to the resulting mixture and heated to 85°–95° C. for 6 hours. The ratio of nickel to aluminum in the mixture is 4:1 and the ratio of carboxylic anion to aluminum is 1:1. A portion of the final slurry was dried and the presence of hydrotalcite-like phase confirmed by X-ray diffraction. Another portion of the final slurry was freeze dried and the sheet morphology confirmed by SEM.

EXAMPLE 5

15.13 g of pseudoboehmite (Versal 850) was slurried in 500 ml of deionized water. 16.3 g of propionic acid was added to the slurry. The suspension was vigorously agitated and heated to 50°–60° C. for 0.5 h. 40.8 g nickel hydroxide along with 1.5 l of deionized water were added to the mixture and heated to 85°–95° C. for 6 hours. The ratio of nickel to aluminum in the mixture is 2:1 and the ratio of carboxylic anion to aluminum is 1:1. A portion of the final slurry was dried and the presence of hydrotalcite-like phase confirmed by X-ray diffraction. Another portion of the final slurry was freeze dried and the sheet morphology confirmed by SEM.

EXAMPLE 6

Figure 3B:
FIG. 3b is a transmission electron microscope picture of the sheet cobalt-hydrotalcite produced according to this invention using acetic acid taken at 50,000× (Example 6).

15.13 g of pseudoboehmite (Versal 850) was slurried in 500 ml of deionized water. 13.7 g of acetic acid was added to the slurry. The suspension was vigorously agitated and heated to 50°–60° C. for 0.5 h. 40.9 g cobalt hydroxide along with 1.5 l of deionized water were added to the resulting mixture and heated to 85°–95° C. for 6 hours, The ratio of cobalt to aluminum in the mixture is 2:1 and the ratio of carboxylic anjou to aluminum is 1:1. A portion of the final slurry was dried and the presence of hydrotalcite-like phase confirmed by X-ray diffraction, TEM was performed on a portion of the slurry to confirm the presence of sheet hydrotalcites (FIG. 3b). Another portion of the slurry was freeze dried and SEM used to determine the average breadth which was 25 micron (FIG. 3a). The surface area of the freeze dried sample, conditioned at 150° C. was 40 $m^2/g$ corresponding to a thickness of 0.02 micron, yielding a breadth to thickness ratio of 1250.

EXAMPLE 7

15.1 g of pseudoboehmite (Versal 850) was slurried in 500 ml of deionized water at 60° C. for 0.5 h. 13.7 g of glacial acetic acid was added to the slurry. 30.7 g of nickel hydroxide and 6.4 g of magnesium hydroxide were added along with 1.5 l of deionized water. The mixture was heated to 95° C. for 6 hours, The ratio of the divalent cation to aluminum in the slurry is 2:1 and the ratio of carboxylic anion to aluminum is 1.0. 25% of the divalent cation was magnesium the rest being nickel. A portion of the final slurry was dried and the presence of hydrotalcite-like phase confirmed by X-ray diffraction. Another portion of the final slurry was freeze dried and the presence of a unique sheet morphology was confirmed by SEM.

EXAMPLE 8

15 g of pseudoboehmite (Versal 850) was slurried in 500 ml of deionized water. 7.92 g of acetic acid was added to the slurry. The suspension was vigorously agitated and heated to 50°–60° C. for 0.5 hour; 40.7 g of cobalt hydroxide along with 1.5 l of deionized water were added to the resulting mixture and heated to 85°–95° C. for 6 hours. The molar ratio of cobalt to aluminum in the mixture was 2:1 and the ratio of carboxylic acid to aluminum was 0.6:1. A portion of the final slurry was dried and the presence of the hydrotalcite-like phase confirmed by X-ray diffraction. Another portion of the final slurry was freeze dried and the sheet morphology confirmed by SEM.

We claim:

1. Hydrotalcite-like material in the form of sheets, said sheets having an average broadness to thickness ratio of about 50:1 to about 5000:1, and having the following formula:

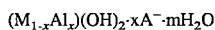

where M is Ni or Co, $A^-$ is a mono carboxylic anion of the form $RCOO^-$ where R is $C_nH_{2n+1}$ and n=0–5, x is a number between 0.2 and 0.4 and m a number between 0 and 4.

2. The hydrotalcite-like material of claim 1 wherein M is substituted up to about 50 mole percent by divalent cations selected from the group consisting of Mg, Ni, Cu, Zn, Co, Mn.

3. The hydrotalcite-like material of claim 1 wherein Al is substituted up to about 50 mole percent by trivalent cations selected from the group consisting of Cr and Fe.

4. The hydrotalcite-like material of claim 1 wherein the sheet broadness to thickness ratio is about 100:1 to about 2000:1.

5. The hydrotalcite-like material of claim 1 wherein the sheet broadness to thickness ratio is about 500–1500.

6. The hydrotalcite-like material of claim 1 where n=0.

7. The hydrotalcite-like material of claim 1 where n=1.

8. The hydrotalcite-like material of claim 1 where n=2.

9. The hydrotalcite-like material of claim 1 where n=3.

10. The hydrotalcite-like material of claim 1 where n=4.

11. The hydrotalcite-like material of claim 1 where n=5.

12. A process for producing hydrotalcite-like material having a sheet like morphology and having an average broadness to thickness ratio ranging from 50 to 5000 and having the following formula:

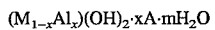

where M is Ni or Co, A is a mono carboxylic anion of the form $RCOO^-$, where R is of the formula $C_nH_{2n+1}$ and n=0–5, x is a number ranging between 0.2 and 0.4 and m is a number between 0 and 4, said process comprising reacting a mixture of divalent metal cations comprising at least 50 mole percent nickel or cobalt cations and trivalent metal cations comprising at least 50 mole percent aluminum cations, said divalent metal cations and trivalent metal cations being present in a ratio of about 1:1 to about 10:1 with mono carboxylic anion having 1–6 carbon atoms, in an aqueous slurry at a temperature of at least 40° C., at a pH from 7 to about 12, and at a ratio of mono carboxylic anion to trivalent metal cation is about 0.1 to about 1.2:1, followed by drying said slurry at a temperature of at least 40° C. to crystallize a hydrotalcite-like material having a sheet-like morphology and having an average broadness to thickness ratio ranging from 50 to 5000.

13. Process of claim 12 wherein the ratio of mono carboxylic anion to trivalent cation is about 0.6:1 to about 1.2:1.

14. The process of claim 12 where nickel hydroxide is the source of nickel.

15. The process of claim 12 where a mono carboxylic salt of nickel is the source of nickel and the mono carboxylic anion.

16. The process of claim 12 wherein acetic acid comprises a source of the mono carboxylic anion.

17. The process of claim 12 where pseudoboehmite is the source of aluminum.

18. The process of claim 12 where sodium aluminate is the source of aluminum.

19. Process of claim 12 wherein the ratio of divalent metal cations to trivalent metal cations is about 2:1 to about 4:1.

20. A process of claim 12 wherein nickel containing hydrotalcite-like material with hexagonal morphology is calcined between 300° and 550° C. and is thereafter used as a source of the nickel and aluminum cations.

21. A process of claim 12 wherein cobalt containing hydrotalcite-like material with hexagonal morphology is calcined between 300° and 550° C. and is thereafter used as a source of the cobalt and aluminum cations.

22. Process of claim 12 wherein the crystallization temperature is about 60° to 100° C.

23. Process of claim 12 wherein the crystallization temperature is about 85° to 95° C.

* * * * *